US011234434B2

(12) United States Patent
Ando et al.

(10) Patent No.: US 11,234,434 B2
(45) Date of Patent: Feb. 1, 2022

(54) METHOD OF CRYOPRESERVATION OF TISSUE DERIVED FROM PLURIPOTENT STEM CELLS

(71) Applicants: SUMITOMO CHEMICAL COMPANY, LIMITED, Tokyo (JP); RIKEN, Wako (JP)

(72) Inventors: Satoshi Ando, Osaka (JP); Tokushige Nakano, Osaka (JP); Yoshiki Sasai, Wako (JP); Mototsugu Eiraku, Wako (JP)

(73) Assignees: SUMITOMO CHEMICAL COMPANY, LIMITED, Tokyo (JP); RIKEN, Wako (JP)

( * ) Notice: Subject to any disclaimer, the term of this patent is extended or adjusted under 35 U.S.C. 154(b) by 0 days.

(21) Appl. No.: 14/360,488

(22) PCT Filed: Nov. 22, 2012

(86) PCT No.: PCT/JP2012/080365
§ 371 (c)(1),
(2) Date: May 23, 2014

(87) PCT Pub. No.: WO2013/077424
PCT Pub. Date: May 30, 2013

(65) Prior Publication Data
US 2014/0342346 A1 Nov. 20, 2014

(30) Foreign Application Priority Data
Nov. 25, 2011 (JP) .............................. JP2011-258208

(51) Int. Cl.
*A01N 1/02* (2006.01)
*C12N 1/04* (2006.01)
(52) U.S. Cl.
CPC ............. *A01N 1/0221* (2013.01); *C12N 1/04* (2013.01)
(58) Field of Classification Search
None
See application file for complete search history.

(56) References Cited

U.S. PATENT DOCUMENTS

| | | | | | |
|---|---|---|---|---|---|
| 4,559,298 | A | * | 12/1985 | Fahy ................................ | 435/1.2 |
| 6,519,954 | B1 | * | 2/2003 | Prien ....................... | A01N 1/02 62/64 |
| 2002/0102239 | A1 | * | 8/2002 | Koopmans ........... | C12N 5/0618 424/93.7 |
| 2004/0096813 | A1 | * | 5/2004 | Baust et al. ........................ | 435/2 |
| 2005/0016198 | A1 | * | 1/2005 | Wowk et al. .................... | 62/371 |
| 2007/0087322 | A1 | | 4/2007 | Eto et al. | |
| 2011/0004304 | A1 | * | 1/2011 | Tao ........................ | C12M 23/16 623/6.63 |
| 2018/0258388 | A1 | * | 9/2018 | Ando .................... | A61K 35/545 |

FOREIGN PATENT DOCUMENTS

| | | |
|---|---|---|
| EP | 0564786 A2 | 10/1993 |
| JP | 2001-247401 A | 9/2001 |
| JP | 2002-325571 A | 11/2002 |
| JP | 2007-105013 A | 4/2007 |
| JP | 2011-036196 A | 2/2011 |
| JP | 4705473 B2 | 6/2011 |
| WO | WO 1995/007611 A1 | 3/1995 |
| WO | WO 2005/045007 A | 5/2005 |
| WO | WO 2008/011070 A2 | 1/2008 |
| WO | WO 2009/051671 A1 | 4/2009 |
| WO | WO 2009/155430 A2 | 12/2009 |
| WO | WO 2011/028524 A1 | 3/2011 |
| WO | WO 2011/047469 A1 | 4/2011 |
| WO | WO 2011/055855 A1 | 5/2011 |

OTHER PUBLICATIONS

Junro et al., JP, 2011-036196A, additional machine translation, translated May 15, 2016, pp. 1-27.*
Eiraku et al., *Nature*, 472: 51-56 (2011).
Kasai et al., *Reproductive BioMedicine Online*, 9(2): 164-170 (2004).
Miyamoto et al., *Experientia*, 42(7): 815-816 (1986).
Nakano et al., *Cell Stem Cell*, 10: 771-785 (2012).
Japanese Patent Office, International Search Report in International Patent Application No. PCT/JP2012/080365 dated (Feb. 19, 2013).
Babaei et al., *Veterinarski Arhiv*, 77(1): 19-27 (2007).
Fahy et al., *Cryobiology*, 21: 407-426 (1984).
Fujioka et al., *International Journal of Developmental Biology*, 48(10):1149-1154 (2004).
Ha et al., *Human Reproduction*, 20(7): 1779-1785 (2005).
Mukaida et al., *Reproductive Biomedicine Online*, 6(2): 221-225 (2003).
Pichugin, "Cryoprotectant solution containing ethylene glycol and dimethyl sulfoxide, used for vitrifying cerebral tissues" (Feb. 5, 2007) [retrieved from internet at URL: http://www.cryonics.org/images/uploads/misc/EG_DMSO.pdf on Apr. 15, 2015].
Sugimoto et al., *Theriogenology*, 53: 1093-1103 (2000).
European Patent Office, Supplementary European Search Report in European Patent Application No. 12851379 dated (Apr. 28, 2015).
The International Bureau of WIPO, International Preliminary Report on Patentability in International Application No. PCT/JP2012/080365 dated (May 27, 2014).
Aramant et al., "Cryopreservation and transplantation of immature rat retina into adult rat retina," *Dev. Brain Res.*, 61(2): 151-159 (1991).

(Continued)

*Primary Examiner* — Laura Schuberg
(74) *Attorney, Agent, or Firm* — Leydig, Voit & Mayer, Ltd.

(57) ABSTRACT

The invention provides a method of cryopreserving a tissue derived from a pluripotent stem cell, including the steps of (1) bringing a tissue derived from a pluripotent stem cell into contact with a cell protection solution that contains sulfoxide and chain polyol, (2) maintaining, in a cryopreservation solution, the pluripotent stem cell-derived tissue that was brought into contact with the cell protection solution in the first step, and (3) cryopreserving, in the presence of a coolant, the pluripotent stem cell-derived tissue that was maintained in the cryopreservation solution.

20 Claims, 5 Drawing Sheets

(56) References Cited

OTHER PUBLICATIONS

European Patent Office, Communication Pursuant to Article 94(3) EPC in European Patent Application No. 12851379.3 dated (Sep. 12, 2017).

Baust et al., "Cryopreservation: An emerging paradigm change," *Organogenesis*, 5(3): 90-96 (2009).

Cao, "Section 10: Experimental Study on Cryopreservation of Tissue Engineered Dermis" in Tissue Engineering (Science Press: 2008), p. 756.

China National Intellectual Property Administration, The First Office Action in Chinese Patent Application No. 201710914871.8 dated (Feb. 3, 2020).

Bakhach, "The cryopreservation of composite tissues: Principles and recent advancement on cryopreservation of different type of tissues," *Organogenesis*, 5(3): 119-126 (2009).

Paynter, "Principles and practical issues for cryopreservation of nerve cells," *Brain Res. Bull.*, 75(1): 1-14 (2008).

\* cited by examiner

A:GFP

B:Chx10

C:Pax6

D:Brn3

DMSO/EG

DMSO/EG/Sucrose

METHOD OF CRYOPRESERVATION OF TISSUE DERIVED FROM PLURIPOTENT STEM CELLS

CROSS-REFERENCE TO RELATED APPLICATIONS

This patent application is the U.S. national phase of International Patent Application No. PCT/JP2012/080365, filed Nov. 22, 2012, which claims the benefit of Japanese Patent Application No. 2011-258208, filed on Nov. 25, 2011, which are incorporated by reference in their entireties herein.

TECHNICAL FIELD

The present invention relates to a cryopreservation method of a tissue derived from a pluripotent stem cell.

BACKGROUND ART

Tissue is a structure of a cell population that has a conformation in which plural types of cells different in the shape and property are sterically configured in a given pattern.

For example, retinal tissue which is one of the constituent elements of eyeball is a membrane-like tissue covering the inner wall at the back of the eyeball, and the retinal tissue has a layer structure wherein nerve cells are aligned regularly. Retina contains five kinds of largely-divided nerve cells of visual cell, bipolar cell, horizontal cell, amacrin cell, and ganglion cell. Light is converted to electric signals by visual cells and the information is transmitted to bipolar cells and horizontal cells via chemical synapses. Bipolar cells form a synaptic connection with amacrin cells and ganglion cells, and the axon of ganglion cell as an optic nerve communicates with the visual center in the cerebrum. For the treatment of retinal disorders, studies of etiology, studies of efficacy and safety in drug discovery, cell transplantation treatment and the like have heretofore been performed. However, a retinal tissue having a layer structure reflecting the human biological tissue, which becomes the material for such studies, is difficult to obtain.

In recent years, production of a retinal tissue comparable to the retinal tissue in a living body by inducing differentiation of pluripotent stem cells such as ES cells has been reported (non-patent document 1). To utilize a tissue obtained by differentiation of pluripotent stem cells for regenerative medicine, safety test and the like, a stable supply of a large amount of the tissue with a uniform quality is essential. On the other hand, production of various tissues by differentiation of pluripotent stem cells requires a given or longer period of differentiation induction, as shown by, for example, a period of not less than 3 weeks for the production of retinal tissue from human ES cells. Also, efficiency of differentiation induction often changes depending on the treatment for the differentiation induction. Therefore, actual practicalization is difficult when such tissue is prepared one by one when in use, and a technique for preserving said tissue at a stage in the process of differentiation induction has been earnestly desired.

DOCUMENT LIST

Non-Patent Document non-patent document 1: M. Eiraku et al., Nature 472, p 51-56 (2011): Self-organizing optic-cup morphogenesis in three-dimensional culture

SUMMARY OF THE INVENTION

Problems to be Solved by the Invention

For a stable supply of a large amount of a tissue derived from pluripotent stem cells for use for regenerative medicine, evaluation of safety and efficacy, and the like, the development of a preservation method of the tissue is urgently needed.

Means of Solving the Problems

The present inventors have conducted intensive studies in view of such situation and found a method of stably preserving a tissue derived from a pluripotent stem cell, which resulted in the present invention.

Accordingly, the present invention provides the following.

[1] A method for cryopreserving a tissue derived from a pluripotent stem cell, comprising the following (1) to (3):
(1) a first step of bringing a tissue derived from a pluripotent stem cell into contact with a cell protection solution that contains sulfoxide and chain polyol,
(2) a second step of maintaining, in a cryopreservation solution, the pluripotent stem cell-derived tissue that was brought into contact with the cell protection solution in the first step,
(3) a third step of cryopreserving, in the presence of a coolant, the pluripotent stem cell-derived tissue that was maintained in the cryopreservation solution in the second step.
[2] The cryopreservation method of the aforementioned [1], wherein the cell protection solution that contains sulfoxide and chain polyol is a cell protection solution that contains sulfoxide, chain polyol and oligosaccharide.
[3] The cryopreservation method of the aforementioned [2], wherein the cell protection solution has a sulfoxide concentration of 5 to 15%, a chain polyol concentration of 4 to 15%, and an oligosaccharide concentration of 5 to 20%.
[4] The cryopreservation method of the aforementioned [2] or [3], wherein the sulfoxide is dimethyl sulfoxide and the chain polyol is ethylene glycol and the oligosaccharide is sucrose.
[5] The cryopreservation method of any of the aforementioned [1] to [4], wherein the aforementioned pluripotent stem cell is a human pluripotent stem cell.
[6] The cryopreservation method of any of the aforementioned [1] to [5], wherein the tissue is a cranial nerve tissue.
[7] The cryopreservation method of any of the aforementioned [1] to [5], wherein the tissue is a retinal tissue.
[8] The cryopreservation method of any of the aforementioned [1] to [7], wherein the third step is performed at a temperature lowering rate of not less than 10° C./min.
[9] The cryopreservation method of any of the aforementioned [1] to [8], wherein the coolant is liquid nitrogen.
[10] The cryopreservation method of any of the aforementioned [1] to [9], wherein the cryopreservation solution is a cryopreservation solution that contains dimethyl sulfoxide, acetamide and propylene glycol.

[11] The cryopreservation method of the aforementioned [10], wherein the concentration of dimethyl sulfoxide is 1 to 4M and the concentration of acetamide is 0.5 to 2M and the concentration of propylene glycol is 1.5 to 6M.
[12] A cell protection solution for cryopreservation of a tissue derived from a pluripotent stem cell, which comprises sulfoxide and chain polyol.
[13] The cell protection solution of the aforementioned [12], which further comprises oligosaccharide.

Effect of the Invention

The present invention enables stable preservation of a tissue derived from a pluripotent stem cell.

MODE(S) FOR CARRYING OUT THE INVENTION

Figure 1:
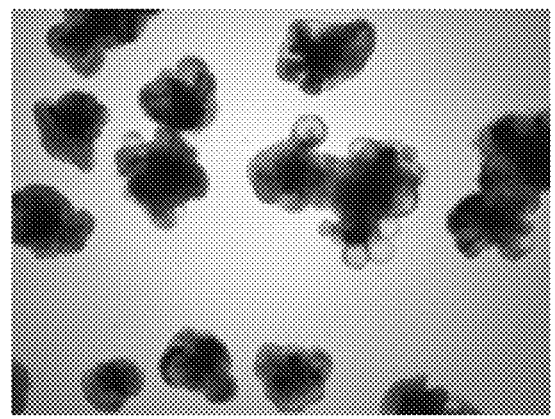
FIG. 1 is a view that shows a light field image of retinal tissues generated in the aggregates obtained by differentiation induction of RAX:: green fluorescent protein (hereinafter, sometimes referred to as "GFP") knock-in human ES cells.

The mode(s) for carrying out the present invention is(are) explained in detail below.

In the present invention, the "transformant" means the entirety or a part of the living matter such as cell produced by transformation. Examples of the transformant include prokaryotic cell, yeast, animal cell, plant cell, insect cell and the like. Depending on the target, the transformant is also sometimes called transformed cell, transformed tissue, transformed host and the like. The cell used in the present invention may also be a transformant.

Examples of the prokaryotic cell used for genetically-engineered technique relating to the present invention include prokaryotic cells belonging to the genus *Escherichia*, the genus *Serratia*, the genus *Bacillus*, the genus *Brevibacterium*, the genus *Corynebacterium*, the genus *Microbacterium*, the genus *Pseudomonas* and the like, specifically, *Escherichia* XL1-Blue, *Escherichia* XL2-Blue, *Escherichia* DH1 and the like. These cells are specifically described in, for example, "Molecular Cloning (3rd edition)" by Sambrook, J and Russell, D. W., Appendix 3 (Volume 3), Vectors and Bacterial strains. A3.2 (Cold Spring Harbor USA 2001).

The "vector" relating to the present invention means a vector capable of transferring a desired polynucleotide sequence into an object cell. Examples of such vector include those capable of autonomous replication in a host cell such as prokaryotic cell, yeast, animal cell, plant cell, insect cell, animal individual and plant individual and the like, or permitting incorporation into a chromosome, and containing a promoter at a position suitable for polynucleotide transcription and the like.

Of such vectors, a vector suitable for cloning is sometimes indicated as a "cloning vector". Such cloning vector generally has multiple cloning sites containing plural restriction enzyme sites. At present, there are many vectors usable for gene cloning in the pertinent field, and they are sold by distributors with different names since they are slightly different (e.g., kind and sequence of restriction enzymes at multi cloning sites). For example, representative ones are described (distributors are also described) in "Molecular Cloning (3rd edition)" by Sambrook, J and Russell, D. W., Appendix 3 (Volume 3), Vectors and Bacterial strains. A3.2 (Cold Spring Harbor USA, 2001), and those of ordinary skill in the art can use them as appropriate according to the object.

The "vector" relating to the present invention also includes "expression vector", "reporter vector", and "recombinant vector". The "expression vector" means a nucleic acid sequence wherein various regulatory elements in addition to a structural gene and a promoter that regulates the expression thereof are operably linked in the host cell. Examples of the "regulatory element" include terminator, selection marker such as a drug resistance gene, and one containing an enhancer, and the like. It is well known to those of ordinary skill in the art that the type of an expression vector of living matter (e.g., animal) and the kind of the regulatory element to be used may vary depending on the host cell.

Examples of the "recombinant vector" relating to the present invention include (a) lambda FIX vector (phage vector) for screening for genome library, (b) lambda ZAP vector (phage vector) for screening for cDNA, (c) pBluescript II SK+/− vector, pGEM vector, pCR2.1 vector (plasmid vector) for cloning of genomic DNA, and the like. Examples of the "expression vector" include pSV2/neo vector, pcDNA vector, pUC18 vector, pUC19 vector, pRc/RSV vector, pLenti6/V5-Dest vector, pAd/CMV/V5-DEST vector, pDON-AI-2/neo vector, pMEI-5/neo vector and the like (plasmid vector) and the like. Examples of the "reporter vector" include pGL2 vector, pGL3 vector, pGL4.10 vector, pGL4.11 vector, pGL4.12 vector, pGL4.70 vector, pGL4.71 vector, pGL4.72 vector, pSLGi vector, pSLO vector, pSLR vector, pEGFP vector, pAcGFP vector, pDsRed vector and the like. These vectors can be utilized as appropriate by reference to the aforementioned Molecular Cloning reference.

In relation to the present invention, examples of the technique for introducing a nucleic acid molecule into a cell include transformation, transduction, transfection and the like. As such introduction techniques, for example, the methods described in Ausubel F. A. et al. ed. (1988), Current Protocols in Molecular Biology, Wiley, New York, N.Y.; Sambrook J. et al. (1987), Molecular Cloning: A Laboratory Manual, 2nd Ed. and 3rd Ed.; Cold Spring Harbor Laboratory Press, Cold Spring Harbor, N.Y.; extra issue, Experimental Medicine "transgene & expression analysis experiment method" YODOSHA CO., LTD., 1997 and the like, and the like can be specifically mentioned. Examples of the technique for confirming intracellular introduction of a gene include Northern blot analysis, Western blot analysis or other well-known conventional techniques and the like.

In relation to the present invention, examples of the introduction method of vector include transfection, transduction, transformation and the like (e.g., calcium phosphate method, liposome method, DEAE-dextran method, electroporation method, method using particle gun (gene gun) etc.).

The cryopreservation method of the present invention is a cryopreservation method characterized by comprising the following (1) to (3):
(1) a first step of bringing a tissue derived from a pluripotent stem cell into contact with a cell protection solution that contains sulfoxide and chain polyol,
(2) a second step of maintaining, in a cryopreservation solution, the pluripotent stem cell-derived tissue that was brought into contact with the cell protection solution in the first step, and
(3) a third step of cryopreserving, in the presence of a coolant, the pluripotent stem cell-derived tissue that was maintained in the cryopreservation solution in the second step.

In the present invention, the "stem cell" refers to a cell that maintains the same differentiation capacity even after cell division, and the cell can regenerate a tissue when the tissue is injured. Here, the stem cell may be an embryonic stem cell (ES cell) or a tissue stem cell (also called tissular stem cell, tissue-specific stem cell or somatic stem cell), or an artificial pluripotent stem cell (iPS cell: induced pluripotent stem cell) but is not limited thereto. As is appreciated from the fact that the above-mentioned stem cell-derived tissue cell can regenerate a tissue, it is known that the stem cell can differentiate into a normal cell close to one in a living body.

Stem cells are available from given organizations, or a commercially available product can also be purchased. For example, human embryonic stem cells, KhES-1, KhES-2 and KhES-3, are available from Kyoto University's Institute for Frontier Medical Sciences. Examples of the mouse embryonic stem cell include EB5 cell and the like.

Stem cells can be maintained by culturing according to a method known per se. For example, stem cells can be maintained by feeder cell-free culture supplemented with fetal calf serum (FCS), Knockout Serum Replacement (KSR), and LIF.

In the present invention, the "pluripotent stem cell" refers to a stem cell that can be cultured in vitro and has an ability to differentiate into any cell (triploblast (ectoderm, mesoderm, endoderm)-derived tissue) constituting a living body except for placenta (pluripotency), including an embryonic stem cell (ES cell). The "pluripotent stem cell" is obtained from fertilized egg, clone embryo, reproductive stem cell, and stem cell in a tissue. It also includes a cell having artificial pluripotency similar to that of embryonic stem cells, after introducing several kinds of genes into a somatic cell (also called artificial pluripotent stem cell). Pluripotent stem cell can be produced by a method known per se. Examples of the production method include the methods described in Cell 131(5) pp. 861-872 (2007), Cell 126(4) pp. 663-676 (2006) and the like.

In the present invention, the "embryonic stem cell (ES cell)" refers to a stem cell having a self replication ability and multipotency (i.e., "pluripotency"), which is a pluripotent stem cell derived from an early embryo. Embryonic stem cell was first established in 1981, and has also been applied to the generation of knockout mouse since 1989. In 1998, a human embryonic stem cell was established, which is also being utilized for regenerative medicine.

In the present invention, the "artificial pluripotent stem cell" refers to a cell induced to have multipotency by directly reprogramming a differentiated cell such as fibroblast etc. by the expression of several kinds of genes such as Oct3/4, Sox2, Klf4, Myc and the like, which was established by Yamanaka et al. in mouse cell in 2006 (Takahashi K, Yamanaka S. Cell. 2006, 126(4), p 663-676). In 2007, it was also established in human fibroblast, and has multipotency similar to that of embryonic stem cells (Takahashi K, Tanabe K, Ohnuki M, Narita M, Ichisaka T, Tomoda K, Yamanaka S. Cell. 2007, 131(5), p 861-872; Yu J, Vodyanik M A, Smuga-Otto K, Antosiewicz-Bourget J, Frane J L, Tian S, Nie J, Jonsdottir G A, Ruotti V, Stewart R, Slukvin I I, Thomson J A., Science. 2007, 318(5858), p 1917-1920; Nakagawa M, Koyanagi M, Tanabe K, Takahashi K, Ichisaka T, Aoi T, Okita K, Mochiduki Y, Takizawa N, Yamanaka S. Nat Biotechnol., 2008, 26(1), p 101-106).

In the present invention, the "differentiation" refers to a phenomenon wherein two or more types of cells having morphologically and/or functionally different qualities are generated in a daughter cell population derived from the division of a single cell. Therefore, the process in which a cell population (cell lineage) derived from a cell having no detectable special characteristics by nature comes to show clear characteristics such as production of a particular protein and the like is also encompassed in the differentiation. It is generally considered at present that cell differentiation is a state of a particular gene group in the genome being expressed, and the cell differentiation can be identified by searching for an intracellular or extracellular factor or condition that causes such gene expression state. In principle, the result of cell differentiation is stable, and differentiation into other type of cell occurs only exceptionally particularly in animal cells.

In the present invention, the "tissue" refers to a structure of a cell population, which has a conformation wherein plural kinds of cells different in the shape and property are sterically configured in a given pattern, and the "tissue derived from a pluripotent stem cell" in the present invention refers to an aggregate of cells obtained by induction of differentiation of a pluripotent stem cell, which is a structure of a cell population, which has a conformation wherein plural types of cells different in the shape and property are sterically configured in a given pattern.

Examples of the cell obtained by induction of differentiation of a pluripotent stem cell include cerebral nerve cell, diencephalic nerve cell, hypothalamus nerve cell, basal nucleus nerve cell, cerebellum nerve cell, intestinal tissue cell, cardiac myocyte, pancreatic cell, hepatic cell, and progenitor cells thereof. Specifically, it can be produced based on WO 2009/148170, J Neurosci. 2011 Feb. 2; 31(5): 1919-33, Nat Neurosci. 2010 October; 13(10): 1171-80, Cell Stem Cell. 2008 Nov. 6; 3(5): 519-32, Proc Natl Acad Sci USA. 2008 Aug. 19; 105(33): 11796-801, Nature. 2011 Feb. 3; 470(7332): 105-9, Nat Biotechnol. 2011 March; 29(3): 267-72, Cell Stem Cell. 2011 Feb. 4; 8(2): 228-40, Development. 2011 March; 138(5): 861-71, Nat Biotechnol. 2006 November; 24(11): 1402-11.

In the present invention, the "cranial nerve tissue" means a structure wherein, in the cerebrum, diencephalic, midbrain, cerebellum and epencephalon of a living body, at least plural kinds of the cells constituting each nerve layer and progenitor cells thereof (for example, in the case of cerebrum, Tbr1 positive cells specific to the 6th layer, Crip2-positive cells specific to the 5th layer, Brn2-positive cells specific to the 2nd-3rd layers and the like) are sterically arranged in layers. As a part of the cranial nerve tissue, a retinal tissue can be mentioned. The "retinal tissue" means a retinal tissue wherein at least plural kinds of cells such as visual cells, horizontal cells, bipolar cells, amacrin cells, retinal ganglion cells, progenitor cells thereof and the like, which constitute respective retinal layers in living retina, are sterically arranged in layers. With regard to each cell, which cell constitutes which retinal layer can be confirmed by a known method, based on the expression of, for example, cell marker (Chx10 (bipolar cell), L7 (bipolar cell), Tuj1 (ganglion cell), Brn3 (ganglion cell), Calretinin (amacrin cell), Calbindin (horizontal-cell), Recoverin (visual cell), Rhodopsin (visual cell), RPE65 (pigment epithelial cell), Mitf (pigment epithelial cell) and the like).

For example, the retinal tissue can be produced by differentiation of human ES cells, specifically, by the methods described in Nature 472, p 51-56 (2011) and WO2011/055855.

In the present invention, the "cryoprotection solution" refers to a mixture of a cryoprotectant and a solvent. The "cryoprotectant" is a substance added to prevent various disorders caused by freezing, in an attempt to maintain the function and survival rate of the cell as much as possible during the cryopreservation of the cells. The cryoprotection solution can be said and means the same as a cell protection solution since it protects cells during freezing.

In the present invention, the cell protection solution (cryoprotection solution) contains sulfoxide and chain polyol as cryoprotectants, and preferably contains sulfoxide, chain polyol and oligosaccharide. To be specific, for example, sulfoxides such as dimethyl sulfoxide (DMSO) and the like; chain polyols such as ethylene glycol, glycerol, propanediol, propylene glycol, butanediol, polyethylene glycol and the like, and preferably further contains oligosaccharides such as sucrose, trehalose, lactose, raffinose and the like. When desired, an amide compound such as acetamide and the like, percoll, ficoll 70, ficoll 70000, polyvinylpyrrolidone and the like may be added.

Examples of the solvent include buffers such as saline, PBS, EBSS, HBSS and the like, culture media for culturing cells, tissues and the like such as DMEM, GMEM, RPMI and the like, serum, serum substitute (Knock Out Serum Replacement: Invitrogen), mixtures thereof and the like.

In the present invention, the final concentration of sulfoxide in a cell protection solution (cryoprotection solution) is, for example, 5 to 15%(w/v), preferably 9 to 13%(w/v), more preferably about 11%(w/v).

In the present invention, the final concentration of chain polyol in a cell protection solution (cryoprotection solution) is, for example, 4 to 15%(w/v), preferably 4.5% to 8%(w/v), more preferably about 5.5%(w/v).

In the present invention, the final concentration of oligosaccharide in a cell protection solution (cryoprotection solution) is, for example, 5 to 20%(w/v), preferably 8 to 12% (w/v), more preferably about 10%(w/v).

In the present invention, the "cryopreservation solution" refers to a medium for cryopreservation of a tissue derived from a pluripotent stem cell. As a cryopreservation solution, commercially available products such as cell BANKER 1, 1plus, 2, 3 (JUJI FIELD INC.), TC-Protector (DS Pharma Biomedical Co., Ltd.), Freezing Medium for human ES/iPS Cells (Reprocell Incorporated), CryoScarless DMSO free (BioVerde), StemCell Keep (BioVerde), EFS solution (NK system) and the like can also be used.

The cryopreservation solution may be a mixture of a cryoprotectant and a solvent. As the cryoprotectant and the solvent, those described above can be mentioned.

The cryopreservation solution in the present invention preferably contains dimethyl sulfoxide, acetamide and propylene glycol.

In the present invention, the concentration of dimethyl sulfoxide in the cryopreservation solution is preferably 1 to 4M, the concentration of acetamide is preferably 0.5 to 2M, and the concentration of propylene glycol is preferably 1.5 to 6M.

The first step of the cryopreservation method of the present invention is a step of bringing a tissue derived from a pluripotent stem cell into contact with a cell protection solution that contains sulfoxide and chain polyol before freezing.

In the above-mentioned first step, a tissue derived from a pluripotent stem cell is brought into contact with a cell protection solution containing sulfoxide and chain polyol.

To "bring a tissue derived from a pluripotent stem cell into contact with a cell protection solution that contains sulfoxide and chain polyol", a tissue derived from a pluripotent stem cell may be transferred into a cell protection solution containing sulfoxide and chain polyol, or a cell protection solution containing sulfoxide and chain polyol may be added to a tissue derived from a pluripotent stem cell.

The time for bringing a tissue derived from a pluripotent stem cell into contact with a cell protection solution containing sulfoxide and chain polyol is, for example, 1 min to 180 min, preferably 5 min to 60 min, more preferably 15 min to 30 min. The temperature at which a tissue derived from a pluripotent stem cell is brought into contact with a cell protection solution containing sulfoxide and chain polyol is, for example, $-10°$ C. to $40°$ C., preferably $0°$ C. to $25°$ C., more preferably $0°$ C. to $8°$ C.

The density of the tissue derived from a pluripotent stem cell in the contact system in the above-mentioned first step (for example, density of the tissue derived from a pluripotent stem cell in the cell protection solution) is, for example, based on the number of aggregates, about 1 to 1000 aggregates/mL, preferably 1 to 100 aggregates/mL. The number of cells per one aggregate is about $10^3$ to $10^6$ cells.

A cell culture vessel used for contacting a cell protection solution is not particularly limited, and can be appropriately determine by those of ordinary skill in the art. Examples of such vessel include flask, tissue culture flask, dish, petri dish, tissue culture dish, multidish, microplate, microwell plate, micropore, multiplate, multiwell plate, chamber slide, schale, tube, tray, culture bag, and roller bottle.

The second step of the cryopreservation method of the present invention is a step of maintaining the tissue derived from a pluripotent stem cell, which was brought into contact with the cell protection solution, in a cryopreservation solution.

In the above-mentioned second step, the tissue derived from a pluripotent stem cell, which was brought into contact with the cell protection solution in the first step, is maintained in a cryopreservation solution.

The density of the tissue derived from a pluripotent stem cell in the cell preservation solution in the above-mentioned second step is, for example based on the number of aggregates, about 1 to 1000 aggregates/mL, preferably 1 to 100 aggregates/mL. The number of cells per one aggregate is about $10^3$ to $10^6$ cells.

The third step of the cryopreservation method of the present invention is a step of cryopreserving the tissue derived from a pluripotent stem cell, which was maintained in the cryopreservation solution, in the presence of a coolant.

As a method for "cryopreserving" tissues and the like, several methods are known. A representative cryopreservation method is, for example, a method involving freezing at a slow rate of 0.1 to 10° C./min for a long time. This method can be performed using apparatuses, tools and the like such as program freezer, BICELL (NIHON FREEZER CO., LTD.) and the like.

As a rapid cryopreservation method, a method involving application of a phenomenon of vitrification that occurs when a crystalline liquid or gas is rapidly solidified at not more than the glass transition temperature without crystallization can be mentioned. This method is superior in that tissue, embryo and ovum immersed in advance in a preservation solution with a high concentration can be stably cryopreserved by a simple operation of vitrification in a short time.

Here, the rapid cryopreservation method is a freezing method of a biological sample, which includes casting the sample into a coolant such as liquid nitrogen and the like. For example, a method involving placing a tissue derived from a pluripotent stem cell and a cryopreservation solution in a cryotube on ice, and immersing the aforementioned cryotube in a coolant with tweezers can be mentioned. The time from maintaining a tissue derived from a pluripotent stem cell in a cryopreservation solution to casting same into a coolant is preferably as short as possible, which is within 30 seconds, preferably within 10 seconds.

The "coolant" to be used in the present invention is preferably one capable of causing vitrification of cells, and a coolant generally at −20° C. or below, preferably −80° C. or below, more preferably −150° C. or below, can be used.

Specific examples of the coolant include liquid nitrogen, slush nitrogen, liquid helium, liquid propane, and ethane sluch, with preference given to liquid nitrogen and slush nitrogen. Slush nitrogen is nitrogen obtained by retaining liquid nitrogen under reduced pressure to lower the liquid nitrogen temperature to −205 to −210° C., which is lower than −196° C. at normal pressure (Huang et al., Human Reproduction, Vol. 20, No. 1, pp. 122-128 (2005)). When slush nitrogen is used as a coolant, preservation by vitrification can be performed by an apparatus such as Vit-Master™ (IMT, Nes Ziona, Israel) and the like.

The temperature lowering rate for cryopreservation in the presence of a coolant is, for example, not less than 10° C./min, preferably not less than 30° C./min, more preferably not less than 50° C./min, particularly preferably not less than 100° C./rain.

The time necessary for cryopreservation in the presence of a coolant to reach a desired cryopreservation temperature (e.g., −196° C. for liquid nitrogen) from ambient temperature is, for example, within 5 min, more preferably within 3 min, further preferably within 1 min.

EXAMPLES

The Examples of the present invention are explained in more detail in the following.
(Establishment of RAX Knock-in Human ES Cells)
Human ES cell line having GFP knocked in the RAX gene locus, which is one of the marker genes of retinal progenitor cells, was prepared.

Zinc Finger Nuclease (ZFN) that specifically cleaves RAX gene on genome DNA of human ES cell line (KhES-1: human ES cell line established by Kyoto University) was purchased from Sigma Aldrich. Using the human ES cells dispersed into single cells, a ZFN endoding mRNA and knock-in vector containing GFP and a drug selective marker, neomycin resistance gene, were co-transfected therein by an electroporation method, and the cells were plated on the neomycin resistance mouse fibroblast which was treated with mitomycin C. The G418 was added to the culture medium on the following day of plating, and drug selection was performed. The colony of the obtained resistance clones was picked up and subsequently cultured, and then knock-in cells were selected by PCR method and Southern blot method resulting in establishment of the RAX::GFP knock-in human ES cell line.
(Induction of Differentiation of RAX Knock-in Human ES Cells into Retinal Tissue)
Using the established RAX::GFP knock-in human ES cells, differentiation into retinal tissue was induced.

RAX::GFP knock-in human ES cells (derived from KhES-1) were cultured according to the method described in "Ueno, M. et al. PNAS 2006, 103(25), 9554-9559" "Watanabe, K. et al. Nat Biotech 2007, 25, 681-686" and used for the experiment.

As the medium, DMEM/F12 medium (Invitrogen) added with 20% KSR (Knockout Serum Replacement; Invitrogen), 0.1 mM 2-mercaptoethanol, 5 to 10 ng/ml bFGF and the like was used. For induction of differentiation into retinal tissue by floating culture, ES cells were dispersed into single cells in 0.25% trypsin-EDTA (Invitrogen), and floated in 150 µl differentiation medium at $9\times10^3$ cells per well of a non-cell adhesive 96 well culture plate (SUMILON spheroid plate, SUMITOMO BAKELITE) to allow for rapid formation of aggregates, which were cultured at 37° C., 5% $CO_2$.

Figure 2:
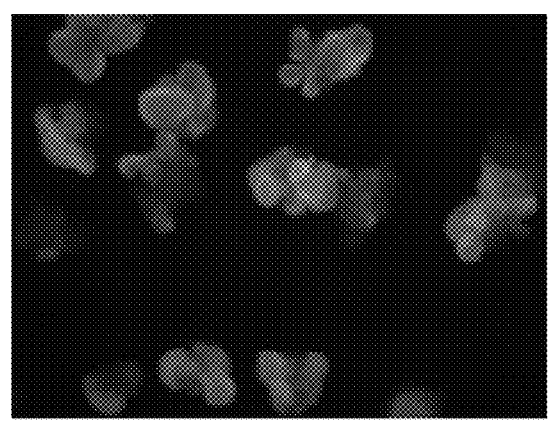
FIG. 2 is a view that shows a fluorescence image of aggregates having the retinal tissue shown in FIG. 1.
Figure 3:
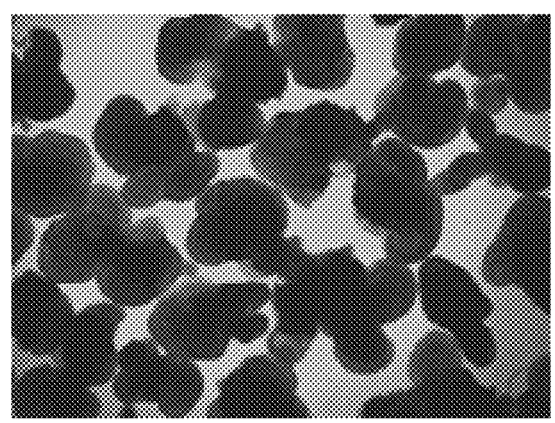
FIG. 3 is a view that shows a light field image of retinal tissues cultured after separation from the aggregates.
Figure 4:
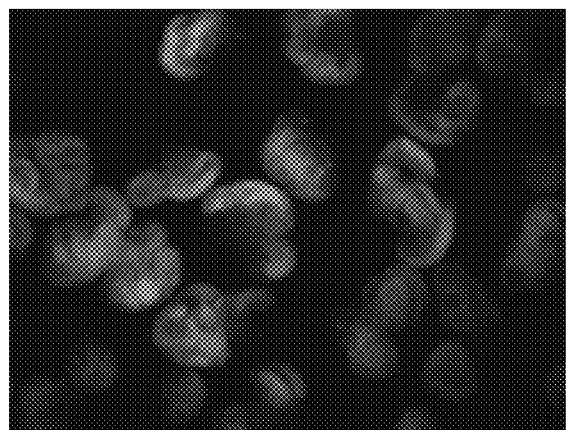
FIG. 4 is a view that shows a fluorescence image of the retinal tissues shown in FIG. 3.
Figure 5:
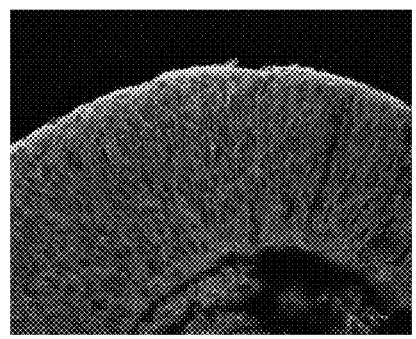
FIG. 5 is a view that shows the results of immunostaining of frozen sections of retinal tissues cultured after separation from the aggregates with anti-GFP antibody, anti-Chx10 antibody, anti-Pax6 antibody, or anti-Brn3 antibody.
Figure 5:
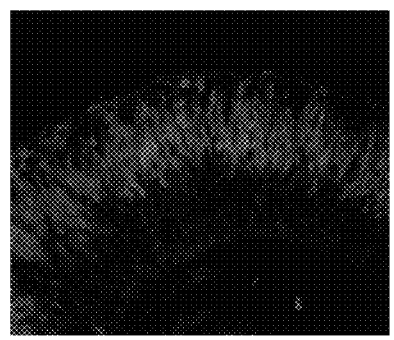
Figure 5:
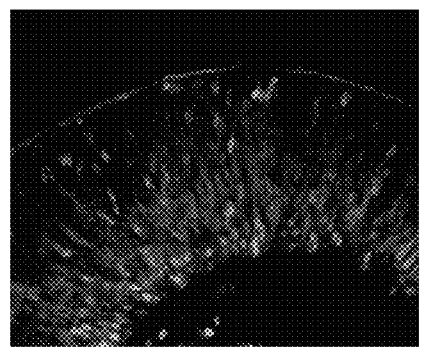
Figure 5:
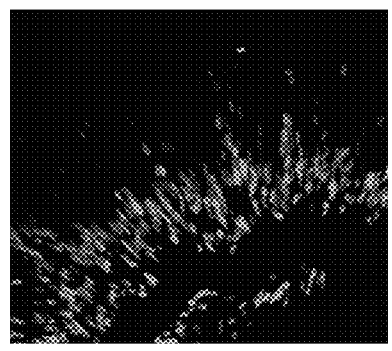

As the differentiation medium therefor, a serum-free medium (G-MEM medium added with 20% KSR, Y27632 and the like) was used. From day 2 of culture, Matrigel was added to the culture. After the start of the differentiation induction, expression of GFP in the aggregates was observed by fluorescence microscopic observation from around day 12 and, on around day 14, a neuroepithelium-like structure expressing GFP was formed on the periphery of the aggregates (FIG. 1, FIG. 2). During the period of from day 18 to day 30, the neuroepithelium-like structure was separated from the aggregates with tweezers, and subsequently cultured in a non-adhesive plastic schale after addition of fetal calf serum and retinoic acid (FIG. 3, FIG. 4). A section was prepared, and the state of differentiation was analyzed by a fluorescence immunostaining method (FIG. 5). For example, it was shown that a neuroepithelial structure after 40 days from the start of the differentiation induction is composed of GFP positive cells expressing RAX gene, and that, in the GFP positive cells, Pax6 which is one of the retinal progenitor cell marker genes positive cell, Chx10 which is one of the bipolar cell marker genes positive cell, and Brn3 which is one of the ganglion cell marker genes positive cell are arranged in layers to form a retinal tissue (FIG. 5).

Comparative Example 1

Figure 6:
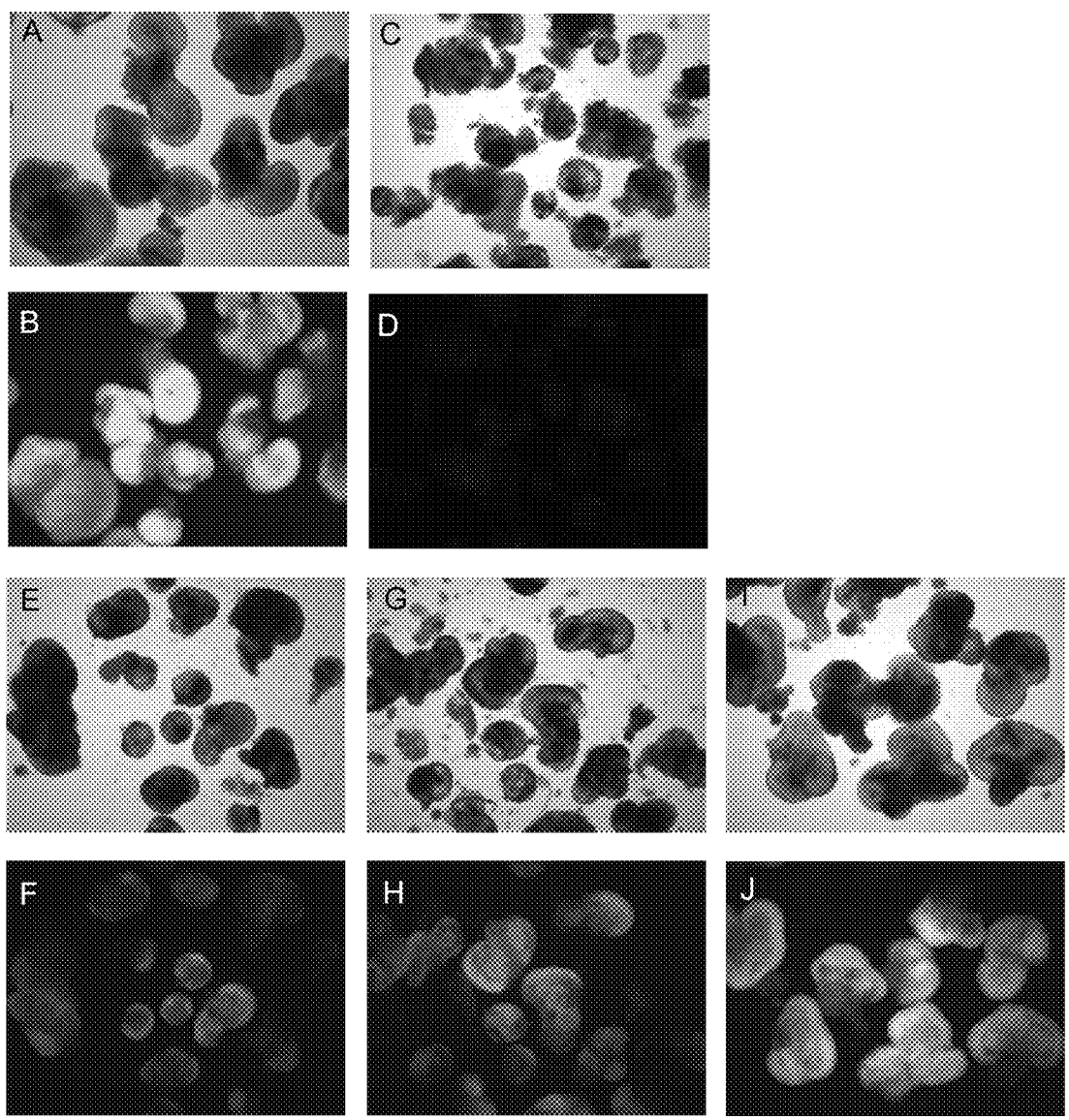
FIG. 6 is a view that shows the state of retinal tissues cultured after separation from the aggregates, which were not frozen as a control of the experiment (A, B), frozen without contact with a cell protection solution (C, D), frozen after a penetration treatment with a solution containing 11.0% (w/v) dimethyl sulfoxide (DMSO) (E, F), frozen after a penetration treatment with a solution containing 11.0% (w/v) dimethyl sulfoxide (DMSO) and 5.55% (w/v) ethylene glycol (G, H), and frozen after a penetration treatment with a solution containing 11.0% (w/v) dimethyl sulfoxide (DMSO), 5.55% (w/v) ethylene glycol and 10% (w/v) sucrose (I, J).

Cryopreservation of Retinal Tissue Obtained by Induction of Differentiation of a Human ES Cell The retinal tissues obtained by differentiation induction were cryopreserved at a temperature lowering rate of not less than 100° C./min.
DMEM/F12 medium added with 2M dimethyl sulfoxide (DMSO), 1M acetamide and 3M propylene glycol (DAP213) was used as a cryopreservation solution. About 10 retinal tissues were collected in a 15 ml polypropylene tube from the culture plate followed by removement of the supernatant and addition of 200 μl of the cryopreservation solution, and the retinal tissue was transferred to a cryotube together with the cryopreservation solution. The cryotube was immediately immersed in liquid nitrogen with tweezers, and cryopreserved at a temperature lowering rate of not less than 100° C./rain. The frozen tube was preserved in a freezer at −150° C. until thawing.
The cryotube was taken out from the freezer at −150° C., and a medium warmed to 37° C. in advance in a 37° C. water bath was added to the cryotube to thaw the tissue. The mixture was dispensed to a 15 ml tube, and the retinal tissue was placed in a medium (10 ml) warmed to 37° C. followed by removement of the supernatant. The tissue was washed with PBS (10 ml) and added to a floating culture dish containing a medium (DMEM/F12 medium added with N2, 10% FBS, retinoic acid and the like) (retinal tissue culture medium), and cultured at 37° C. A microscopic observation and fluorescence microscopic observation were performed from the following day of thawing, and the cell survival state and the appearance of the epithelial structure were compared with those of the retinal tissue (FIG. 6 A, B) free of cryopreservation, and success or failure of the cryopreservation was checked.
As a result, almost all cells were dead, and a lot of debris of the dead cells was observed. The expression of GFP was scarcely observed. Therefore, it was shown that mere cryopreservation at a temperature lowering rate of not less than 100° C./min does not result in the cryopreservation of the retinal tissue (FIG. 6 C, D).

Comparative Example 2

Cryopreservation of Retinal Tissue Obtained by Induction of Differentiation of a Human ES Cell by Freezing after Penetration Treatment in Cryoprotectant (11.0% (w/v) Dimethyl Sulfoxide (DMSO)

Before freezing, a retinal tissue obtained by induction of differentiation was subjected to a penetration treatment in a solution containing dimethyl sulfoxide (DMSO) as a cryoprotectant, and cryopreserved at a temperature lowering rate of not less than 100° C./rain.
About 10 to 20 retinal tissues were collected in a 15 ml polypropylene tube from the culture plate followed by removement of the supernatant and addition of a solution (1 ml) containing a cryoprotectant cooled in advance on ice, and the mixture was stood on ice for 15 min to 30 min. As the solution containing a cryoprotectant, the aforementioned retinal tissue culture medium added with 11.0% (w/v) dimethyl sulfoxide (DMSO) was used. The solution containing a cryoprotectant was removed, DAP213 (200 μl) was added as a cryopreservation solution, and the retinal tissue was transferred to a cryotube together with the cryopreservation solution. The cryotube was immediately immersed in liquid nitrogen with tweezers, and cryopreserved at a temperature lowering rate of not less than 100° C./min. The frozen tube was preserved in a freezer at −150° C. until thawing.
When cryopreserved at a temperature lowering rate of not less than 100° C./min after a penetration treatment using a retinal tissue culture medium containing 11.0% (w/v) dimethyl sulfoxide (DMSO) as a cryoprotectant, the retinal tissue expressing RAX drastically reduced as compared to the control without freezing (FIG. 6 E, F).

Example 1

Cryopreservation of Retinal Tissue Obtained by Induction of Differentiation of a Human ES Cell, by Freezing after Penetration Treatment with Cryoprotectants (11.0% (w/v) Dimethyl Sulfoxide (DMSO) and 5.55% (w/v) Ethylene Glycol)

Performed in the same manner as in Comparative Example 2 except that a retinal tissue obtained by differentiation induction was subjected to a penetration treatment using a solution containing 11.0% (w/v) dimethyl sulfoxide (DMSO) and 5.55% (w/v) ethylene glycol (EG) as cryoprotectants.
When cryopreserved at a temperature lowering rate of not less than 100° C./min after a cryoprotectant penetration treatment using a retinal tissue culture medium containing 11.0% (w/v) dimethyl sulfoxide (DMSO) and 5.55% (w/v) ethylene glycol (EG), the preserving property of a retinal tissue expressing RAX was improved (FIG. 6 G, H) and the layer structure was found to have been maintained (FIG. 8 A, B), relative to the aforementioned cryoprotectant penetration treatment using a retinal tissue culture medium containing 11.0% (w/v) dimethyl sulfoxide (DMSO).

Example 2

Cryopreservation of Retinal Tissue Obtained by Induction of Differentiation of a Human ES Cell, by Freezing after Penetration Treatment with Cryoprotectants (11.0% (w/v) Dimethyl Sulfoxide (DMSO), 5.55% (w/v) Ethylene Glycol (EG) and 10% (w/v) Sucrose)

Figure 8:
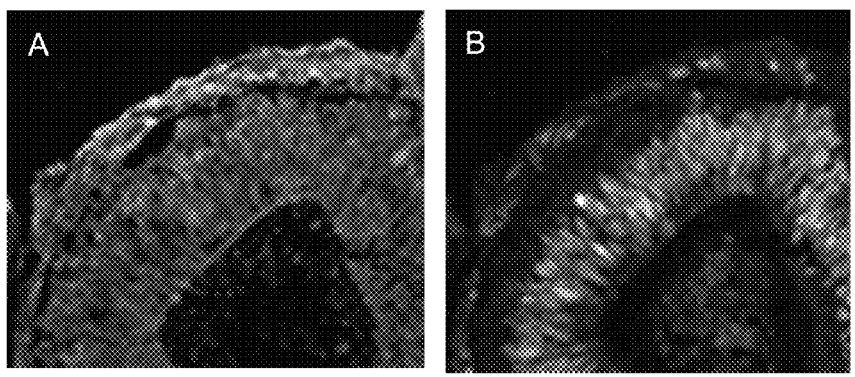
FIG. 8 is a view that shows the results of immunostaining with anti-GFP antibody (A, C, E), anti-Chx10 antibody (B), anti-Chx10 and anti-Pax6 antibody (D), anti-Chx10 and anti-TuJ1 antibody (F) of frozen sections of the retinal tissues cultured after separation from the aggregates, which were frozen after a penetration treatment with a solution containing 11.0% (w/v) dimethyl sulfoxide (DMSO) and 5.55% (w/v) ethylene glycol (A, B) and a penetration treatment with a solution containing 11.0% (w/v) dimethyl sulfoxide (DMSO), 5.55% (w/v) ethylene glycol and 10% (w/v) sucrose (C, D, E, F).
Figure 8:
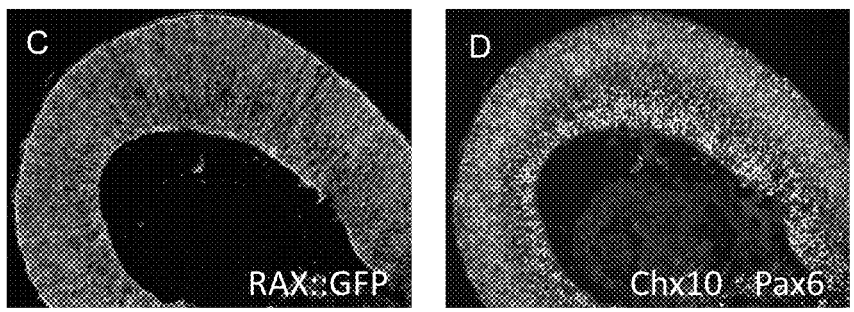
Figure 8:
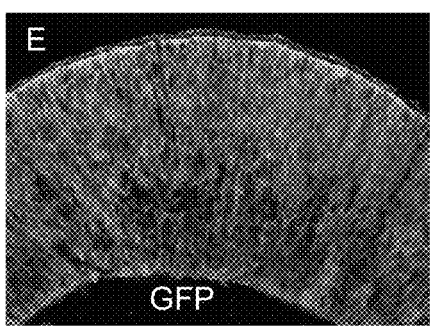
Figure 8:
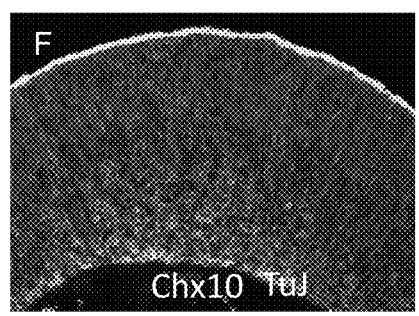

Performed in the same manner as in Comparative Example 2 except that a retinal tissue obtained by differentiation induction was subjected to a penetration treatment using a solution containing 11.0% (w/v) dimethyl sulfoxide (DMSO), 5.55% (w/v) ethylene glycol (EG) and 10% (w/v) sucrose as cryoprotectants.
When cryopreserved at a temperature lowering rate of not less than 100° C./min after a cryoprotectant penetration treatment using a retinal tissue culture medium containing 11.0% (w/v) dimethyl sulfoxide (DMSO), 5.55% (w/v) ethylene glycol (EG) and 10% (w/v) sucrose, the condition comparable to a retinal tissue without cryopreservation was maintained while the intensity of GFP expression was somewhat weak as compared to the retinal tissue without cryopreservation. The preservation property was very good (FIG. 6 I, J), and the layer structure was also maintained (FIG. 8 C, D, E).

Comparative Example 3

Cryopreservation of Retinal Tissue Obtained by Induction of Differentiation of a Human ES Cell, by Freezing after Penetration Treatment with Cryoprotectant (Sucrose)

Using the aforementioned retinal tissue culture media respectively added with 5% sucrose, added with 10% sucrose, added with 20% sucrose, added with 5.55% EG and 10% sucrose, and added with 11% (w/v) dimethyl sulfoxide (DMSO) and 10% (w/v) sucrose as cryoprotectant penetration solutions, freezing and thawing were performed by processes similar to those mentioned above.

Figure 7:
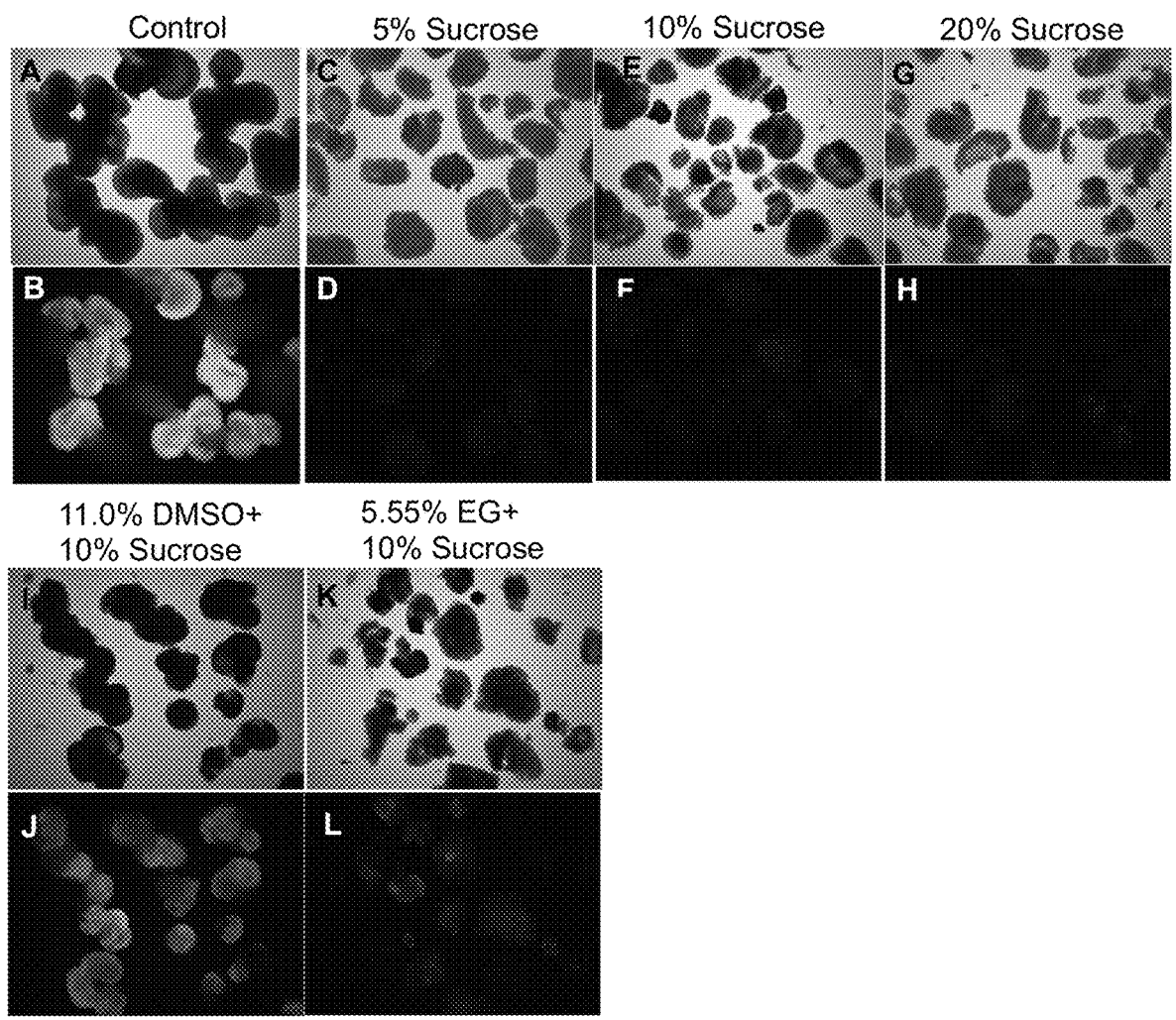
FIG. 7 is a view that shows the state of retinal tissues cultured after separation from the aggregates, which were not frozen as a control of the experiment (A, B), frozen after a penetration treatment with a solution containing 5% (w/v) sucrose (C, D), frozen after a penetration treatment with a solution containing 10% (w/v) sucrose (E, F), frozen after a penetration treatment with a solution containing 20% (w/v) sucrose (G, H), frozen after a penetration treatment with a solution containing 11.0% (w/v) dimethyl sulfoxide (DMSO) and 10% (w/v) sucrose (I, J), frozen after a penetration treatment with a solution containing 5.55% (w/v) ethylene glycol and 10% (w/v) sucrose (K, L).

When cryopreserved at a temperature lowering rate of not less than 100° C./min after a penetration treatment using a retinal tissue culture medium added with sucrose alone as a cryoprotectant penetration solution, the cell survival property after thawing was considerably poor at any concentration of 5% (w/v), 10% (w/v) and 20% (w/v) and GFP expression was scarcely observed (FIG. 7 C, D, E, F, G, H), as compared to a control free of freezing (FIG. 7 A, B). Also, when cryopreserved at a temperature lowering rate of not less than 100° C./min after a penetration treatment using a retinal tissue culture medium containing 5.55% (w/v) EG and 10% (w/v) sucrose, the cell survival property after thawing was considerably poor and GFP expression was scarcely observed (FIG. 7 K, L), as compared to a control free of freezing. When cryopreserved at a temperature lowering rate of not less than 100° C./min after a penetration treatment using a retinal tissue culture medium containing 11.0% (w/v) dimethyl sulfoxide (DMSO) and 10% (w/v) sucrose, the cell survival property after thawing was poor and GFP expression was weak, as compared to a control free of freezing, and preservation in a state comparable to a control without freezing was not possible (FIG. 7 I, J).

INDUSTRIAL APPLICABILITY

According to the present invention, a preservation method of a tissue derived from a pluripotent stem cell can be provided.

This application is based on a patent application No. 2011-258208 filed in Japan (filing date: Nov. 25, 2011), the contents of which are incorporated in full herein.

The invention claimed is:

1. A method for cryopreserving a retinal tissue having a layer structure, comprising
(1) a first step of bringing the retinal tissue having a layer structure, wherein the retinal tissue is a RAX gene-expressing neuroepithelial structure obtained by in vitro induction of differentiation of a pluripotent stem cell and comprises a Pax6-positive cell layer, a Chx10-positive cell layer, and a Brn3-positive cell layer, into contact at 0° C. to 8° C. with a first solution that is a cell protection solution comprising 5 to 15% (w/v) dimethyl sulfoxide and 4 to 15% (w/v) ethylene glycol for a penetration treatment,
(2) a second step of bringing the retinal tissue that was brought into contact with the cell protection solution in the first step into contact with a second solution that is a cryopreservation solution, wherein the cell protection solution is removed prior to contact with the cryopreservation solution, and
(3) a third step of cryopreserving the retinal tissue that was brought into contact with the cryopreservation solution in the second step, thereby obtaining a cryopreserved retinal tissue having a layer structure in which the layer structure is maintained in a state comparable to a retinal tissue without cryopreservation, wherein the cryopreserving step is performed immediately after the start of the second step.

2. The cryopreservation method according to claim 1, wherein the cell protection solution further comprises an oligosaccharide.

3. The cryopreservation method according to claim 1, wherein the cell protection solution has an oligosaccharide concentration of 5 to 20% (w/v).

4. The cryopreservation method according to claim 2, wherein the oligosaccharide is sucrose.

5. The cryopreservation method according to claim 4, wherein the cell protection solution has a dimethyl sulfoxide concentration of 11% (w/v), an ethylene glycol concentration of 5.55% (w/v), and a sucrose concentration of 10% (w/v).

6. The cryopreservation method according to claim 1, wherein the pluripotent stem cell is a human pluripotent stem cell.

7. The cryopreservation method according to claim 1, wherein the third step is performed at a temperature lowering rate of 0.1 to 10° C/min.

8. The cryopreservation method according to claim 1, wherein the third step is performed at a temperature lowering rate of not less than 10° C/min.

9. The cryopreservation method according to claim 1, wherein the third step is performed in the presence of a coolant.

10. The cryopreservation method according to claim 9, wherein the coolant is liquid nitrogen.

11. The cryopreservation method according to claim 1, wherein the cryopreservation solution comprises dimethyl sulfoxide, acetamide, and propylene glycol.

12. The cryopreservation method according to claim 11, wherein the concentration of dimethyl sulfoxide is 1M to 4M, the concentration of acetamide is 0.5M to 2M, and the concentration of propylene glycol is 1.5M to 6M.

13. The cryopreservation method according to claim 1, wherein the tissue comprises about $10^3$ to $10^6$ cells.

14. The cryopreservation method according to claim 13, wherein the tissue is brought into contact with the cell protection solution in the first step in a density of about 1 to 100 tissues/mL.

15. The cryopreservation method according to claim 1, wherein the retinal tissue having a layer structure comprises more than one kind of cells selected from the group consisting of visual cells, horizontal cells, bipolar cells, amacrin cells, retinal ganglion cells, and progenitor cells thereof.

16. The cryopreservation method according to claim 1, wherein the cell protection solution has a dimethyl sulfoxide concentration of 11% (w/v) and an ethylene glycol concentration of 5.55% (w/v).

17. A method of obtaining a retinal tissue having a layer structure comprising
(1) a first step of bringing the retinal tissue having a layer structure, wherein the retinal tissue is a RAX gene-expressing neuroepithelial structure obtained by in vitro induction of differentiation of a pluripotent stem cell and comprises a Pax6-positive cell layer, a Chx10-positive cell layer, and a Brn3-positive cell layer, into contact at 0° C. to 8° C. with a first solution that is a cell protection solution comprising 5 to 15% (w/v) dimethyl sulfoxide and 4 to 15% (w/v) ethylene glycol for a penetration treatment, (2) a second step of bringing the retinal tissue that was brought into contact with the cell protection solution in the first step into contact with a second solution that is a cryopreservation solution, wherein the cell protection solution is removed prior to the contact with the cryopreservation solution, (3) a third step of cryopreserving the retinal tissue that was brought into contact with the cryopreservation solution in the second step thereby obtaining a cryopreserved retinal tissue having a layer structure in which the layer structure is maintained, wherein the cryopreserving step is performed immediately after the start of the second step, and (4) a fourth step of thawing the cryopreserved retinal tissue obtained in the third step thereby obtaining a retinal tissue having a layer structure in which the layer structure is maintained in a state comparable to a retinal tissue without cryopreservation.

18. The method according to claim 17, wherein the cell protection solution has a dimethyl sulfoxide concentration of 11% (w/v) and an ethylene glycol concentration of 5.55% (w/v).

19. The method according to claim 18, wherein the cell protection solution further comprises 10% (w/v) sucrose.

20. A method for maintaining a conformation of retinal tissue having a layer structure during cryopreservation, comprising (1) a first step of bringing a retinal tissue having a layer structure, which is obtained by in vitro induction of differentiation of a pluripotent stem cell and comprises a Pax6 positive cell layer, a Chx10 positive cell layer and a Brn3 positive cell layer, into contact at 0° C. to 8° C. with a first solution that is a cell protection solution comprising 5 to 15% (w/v) dimethyl sulfoxide and 4 to 15% (w/v) ethylene glycol for a penetration treatment, (2) a second step of bringing the retinal tissue that was brought into contact with the cell protection solution in the first step into contact with a second solution that is a cryopreservation solution, wherein the cell protection solution is removed prior to contact with the cryopreservation solution, and (3) a third step of cryopreserving the retinal tissue that was brought into contact with the cryopreservation solution in the second step, thereby obtaining a cryopreserved retinal tissue having a layer structure in which the layer structure is maintained in a state comparable to a retinal tissue without cryopreservation, wherein the cryopreserving step is performed immediately after the start of the second step.

* * * * *